United States Patent
Lin et al.

Patent Number: 6,148,056
Date of Patent: Nov. 14, 2000

[54] EFFICIENT CONE-BEAM RECONSTRUCTION SYSTEM USING CIRCLE-AND-LINE ORBIT DATA

[75] Inventors: Wen-Tai Lin, Schenectady; Mehmet Yavuz, Clifton Park, both of N.Y.

[73] Assignee: General Electric Company, Schenectady, N.Y.

[21] Appl. No.: 09/253,706

[22] Filed: Feb. 22, 1999

[51] Int. Cl.[7] .................................................. A61B 6/03
[52] U.S. Cl. ................................................. 378/4; 378/901
[58] Field of Search .................................... 378/4, 15, 901

[56] References Cited

U.S. PATENT DOCUMENTS 5,706,325   1/1998   Hu ................................................ 378/4

OTHER PUBLICATIONS

Hui Hu, "A Cone Beam Reconstruction Algorithm For The Circular Orbit And The Circle–And–Line Orbit", Jan. 31, 1997, Applied Science Lab., GE Medical Systems, PO Box 414 NB–922, Milwaukee, WI 53201, pp. 1–24.

LA Feldkamp, LC Davis, JW Kress, "Practical Cone–Beam Algorithm", J. Opt. Soc. Am. A/vol. 1, No. 6/Jun., 1984, pp. 612–619.

*Primary Examiner*—David V. Bruce
*Attorney, Agent, or Firm*—Jill M. Breedlove; Douglas E. Stoner

[57] ABSTRACT

A system is provided for reconstructing x-ray tomographic images based upon the circle-and-line orbit. The system includes the steps of combining, in the frequency domain, images reconstructed separately from the circular and linear orbit data. Specifically, the method involves the steps of (1) converting the shadow zone into a shadow cone in frequency domain, (2) mapping the shadow cone in 3D Fourier space onto a set of 2D Fourier planes, (3) removing data lying within the region marked as the projection of the shadow cone from the Fourier transform of the circular orbit data and patching the same from the Fourier transform of the line orbit data, (4) transforming each 2D Fourier plane into a respective 2D image plane, and (5) converting the horn-shaped volume back to a grid volume. An interpolation technique is also provided for reconstructing the line orbit data using a Direct Fourier method (DFM).

19 Claims, 5 Drawing Sheets

EFFICIENT CONE-BEAM RECONSTRUCTION SYSTEM USING CIRCLE-AND-LINE ORBIT DATA

BACKGROUND OF THE INVENTION

The field of the invention relates to computer tomography and more particularly to x-ray medical computer tomography.

Computer tomography (CT) using cone-beam projection technology typically employs an x-ray source to form a vertex in the shape of a cone. A scanning orbit of the x-ray source is a curve along which the vertex of the cone beam moves during a scan. A set of detectors are disposed at a fixed distance from the cone-beam source. Methods currently exist which have established a relationship between cone-beam projections and a first derivative of the three dimensional (3D) Radon transforms of such projections. Theoretically, each source position "S" can deliver Radon data positioned on a sphere, the Radon shell of "S." The corresponding spheres on a circular orbit sweep out the Radon space of the object, referred to as a torus. Regions inside the smallest sphere containing the object, but exterior to the torus, is called the shadow zone. The shadow zone characterize the region where Radon data is missing from the circular orbit.

When using a circle-and-line orbit, the line-orbit data is typically used for filling in the shadow zone. Even though the shadow zone is very small, as compared to the volume of the entire valid Radon data delivered by the circular orbit, current cone-beam projection techniques are computationally intensive. Accordingly, a need exists for simplifying image reconstruction based on the circle-and-line orbit.

BRIEF SUMMARY OF THE INVENTION

A system is provided for reconstructing x-ray tomographic images based upon the circle-and-line orbit. The system includes the steps of combining, in the frequency domain, images reconstructed separately from the circular and linear orbit data. Specifically, the method involves the steps of (1) converting the shadow zone into a shadow cone in the frequency domain, (2) mapping the shadow cone in 3D Fourier space onto a set of 2D Fourier planes, (3) removing data lying within the region marked as the projection of the shadow cone from the Fourier transform of the circular orbit data and patching the same from the Fourier transform of the line orbit data, (4) transforming each 2D Fourier plane into a respective 2D image plane, and (5) converting the horn-shaped volume back to a grid volume. An interpolation technique is also provided for reconstructing the line orbit data using a Direct Fourier Method (DFM).

DETAILED DESCRIPTION OF THE INVENTION

Figure 1:
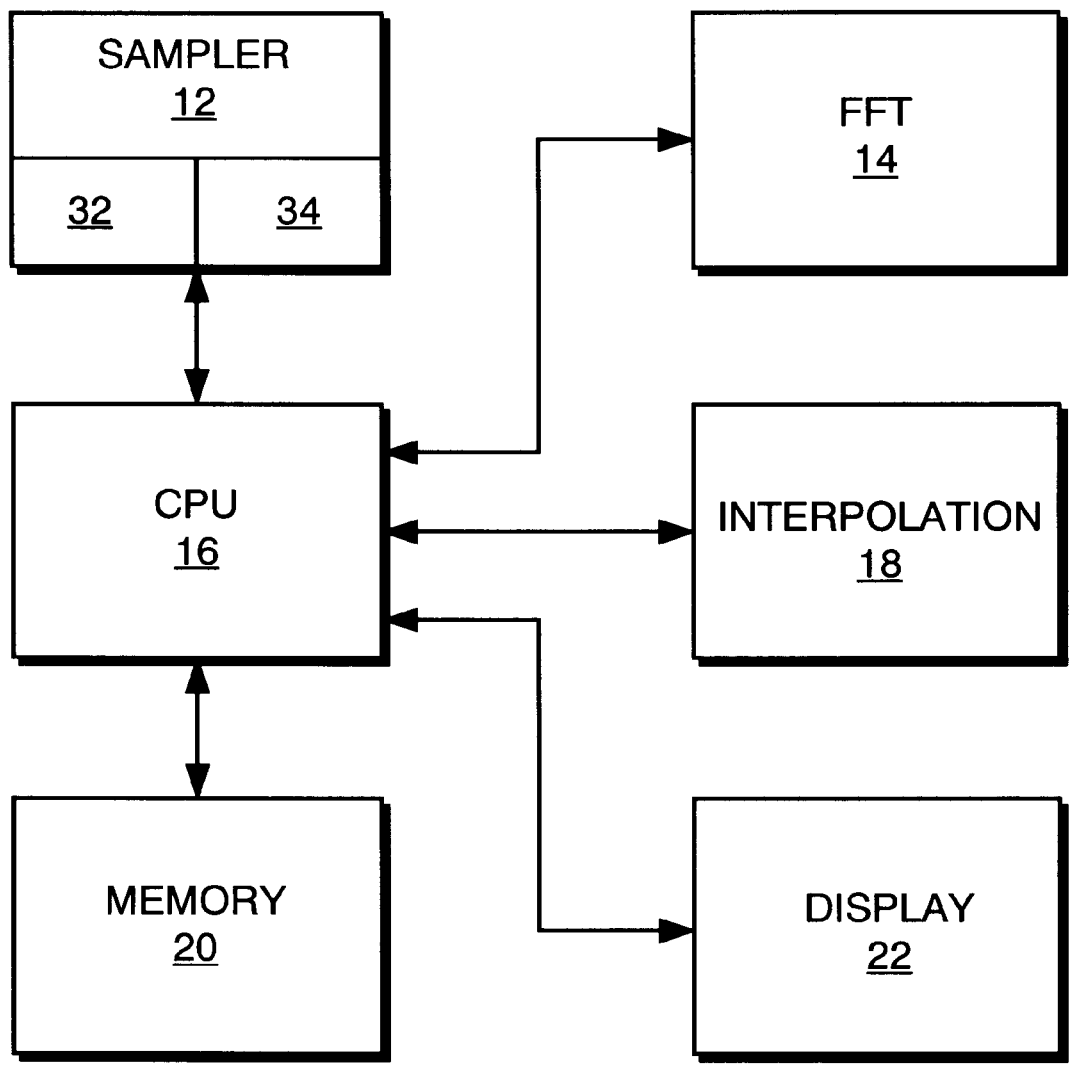
FIG. 1 depicts an x-ray tomography imaging system of the present invention.

FIG. 1 depicts a CT imaging system 10, generally, in accordance with an illustrated embodiment of the invention. Included within the system 10 is a central processing unit (CPU) 16, a sampling device 12, and other image support and processing subsystems 14, 18, 20, 22. The sampling device 12 includes an x-ray source 34 and an image detecting array 32 along with actuating devices. The image support devices 14, 18, 22 include a Fast Fourier processor 14, an interpolator 18, a memory 20, and a display 22.

In two dimensional (2D) tomographic reconstruction one alternative to Filtered Back Projection (FBP) is Direct Fourier Method (DFM) back projection. Direct Fourier Method back projection is based on the projection slice theorem, which postulates that a one dimensional (1D) Fourier Transform (FT) of a projection at a specific angle corresponds to the cross section of the 2D FT of the object at the same angle. DFM shall be used as an alternative to the conventional back-projection reconstruction involving the line orbit.

In a CT system 10, (FIG. 1) using circular orbit data and alternatively the circle and line orbit data which is to be reconstructed, represented in the function defined by $f(\vec{r})$, can be expressed by the following equation:

$$f(\vec{r}) = f_{c0}(\vec{r}) + f_{c1}(\vec{r}) + f_l(\vec{r}).$$

The first two elements, $f_{c0}(\vec{r})$ and $f_{c1}(\vec{r})$, are evaluated using circularly-scanned data and techniques (e.g., as given by Feldkamp et al. and Hu). For example, Feldkamp et al. has published cone-beam algorithms in a paper entitled, PRACTICAL CONE-BEAM ALGORITHM, published in the Journal of the Optical Society of America, Vol. 1, No. 6, June 1984, pages 612–619, herein incorporated by reference. The second element is needed only when the third term is evaluated in the Radon space. Since we will evaluate the third term in the Fourier space, thus the second term will be ignored.

Figure 2:
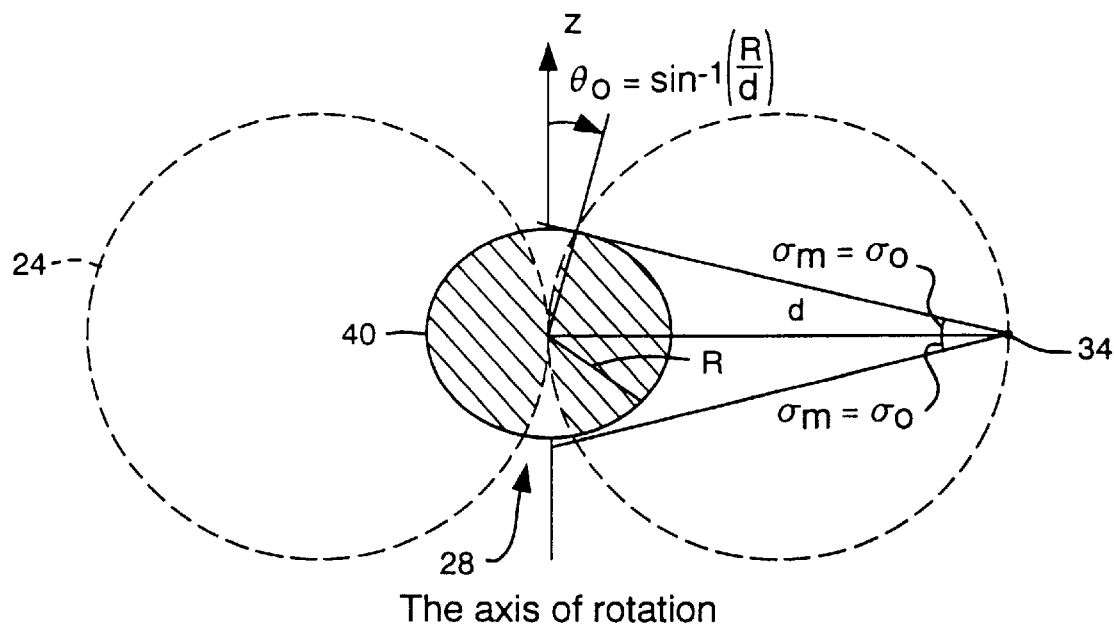
FIG. 2 depicts a cross-section of the circular orbit formed by the system of FIG. 1.

The third element, $f_1(\vec{r})$, is evaluated from the linear orbit data. It is typically used for filling in a shadow zone 28 defined by a torus 24, which is swept out by the circular orbit about the axis of rotation, and the smallest sphere containing the object 40 (FIG. 2). Even though this shadow zone 28, which is defined in Radon space, is small as compared to the torus 24, the current back-projection process is computationally intensive, as is apparent from the complexity of $f_1(\vec{r})$ as defined, for example in a paper by Hui Hu, entitled, CONE BEAM RECONSTRUCTION ALGORITHM FOR THE CIRCULAR ORBIT AND A CIRCLE-AND-LINE ORBIT, published by the Applied Science Laboratory, GE Medical Systems, Jan. 31, 1997, herein incorporated by reference, in equation 1 listed below.

$$f_l(\vec{r}) = -\frac{1}{4\pi^2(d+\vec{r}\cdot\hat{x}')}\int dz_o \int_{\Theta=0}^{\pi} d\Theta H(z_o, \Theta, l)_{l=Y_o\sin\Theta+Z_o\cos\Theta}. \quad (1)$$

where $$H(z_o, \Theta, l) = \cos\Theta w(z_o, \Theta, l)\left(\frac{d^2+l^2}{d^2}\frac{\delta^2\Sigma_{z_o}(l,\Theta)}{\delta^2 l} + \frac{2l}{d^2}\frac{\delta\Sigma_{z_o}(l,\Theta)}{\delta l}\right),$$

$$\Sigma_{z_o}(l,\Theta) = \int\int P_{z_o}(Y,Z)\delta(Y\sin\Theta+Z\cos\Theta-l) dY dZ,$$

$$w(z_o, \Theta, l) = \begin{cases} 1 & \text{when } 2lz_o\cos\Theta+z_o^2\cos^2\Theta-d^2\sin^2\Theta > 0 \\ 0 & \text{otherwise} \end{cases},$$

and where $H(z_o,\Theta,l)$ is the weighted second derivative of Radon data computed from a snapshot incurred at $z=z_o$. For each point in the object space, $\vec{r}$, the point is associated with a point $(Y_o, Z_o)$ on the detector plane. If a circle is drawn on the detector plane using the origin (0, 0) and $(Y_o, Z_o)$ as two ends of a diameter, then all the valid Radon data, $H(z_o, \Theta, l)$, intercepted by the circle satisfy the constraint: $l=Y_o \sin \Theta + Z_o \cos \theta$. For each point $(Y_o, Z_o)$, there is a corresponding set of Radon data, $H(z_o,\Theta,l)$, to be summed and then back-projected onto the object space. The computational complexity of this process is thus close to $O(N^5)$.

Figure 3:
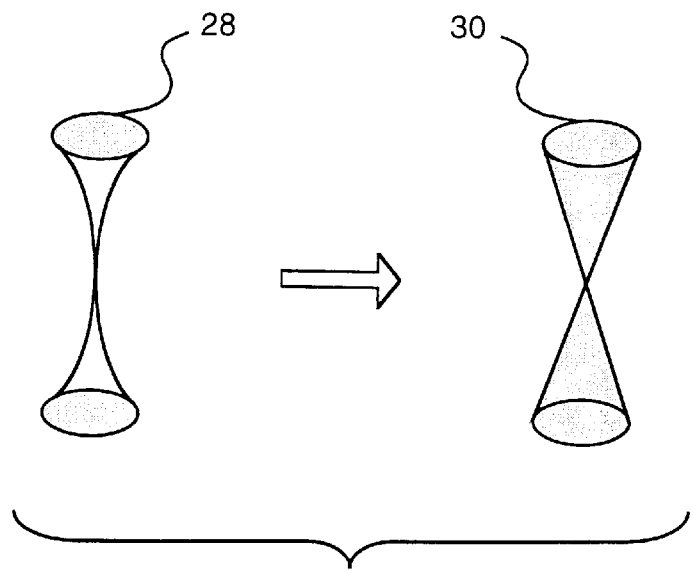
FIG. 3 depicts a shadow zone of FIG. 2 and corresponding shadow cone.

The present invention describes a method for determining a computational efficient CT reconstruction using data obtained from a line orbit scan of the object 40 (illustrated in FIG. 2). First, the shadow zone 28 in Radon space is augmented and converted into a shadow cone 30 in frequency space (FIG. 3). Secondly, the patching process performed by CPU 16 is simplified from the original three-dimensional frequency space into multiple 2D frequency slices.

The first step is based on the fact that the Fourier transform of a radial line in 3D Radon space is equivalent to the same radial line in 3D Fourier space. If a radial line in 3D Radon space intercepts the shadow zone 28, then its counterpart in the 3D Fourier space is "contaminated" because some Radon data in the radial Radon line has been missing. Since all the radial lines intercepting the shadow zone 28 form a shadow cone 30, the collection of their counterparts in the 3D Fourier space also form a frequency-insufficient cone. The frequency-insufficient cone (or the contaminated cone) of the first term of equation (1), which is defined in Fourier space, will be replaced by that of the third term of equation (1).

The second step is to show that the linear orbit supports enough frequency data to replace the contaminated cone (which is due to the circular orbit), followed by a procedure for replacing the contaminated cone in 2D Fourier space.

Figure 5:
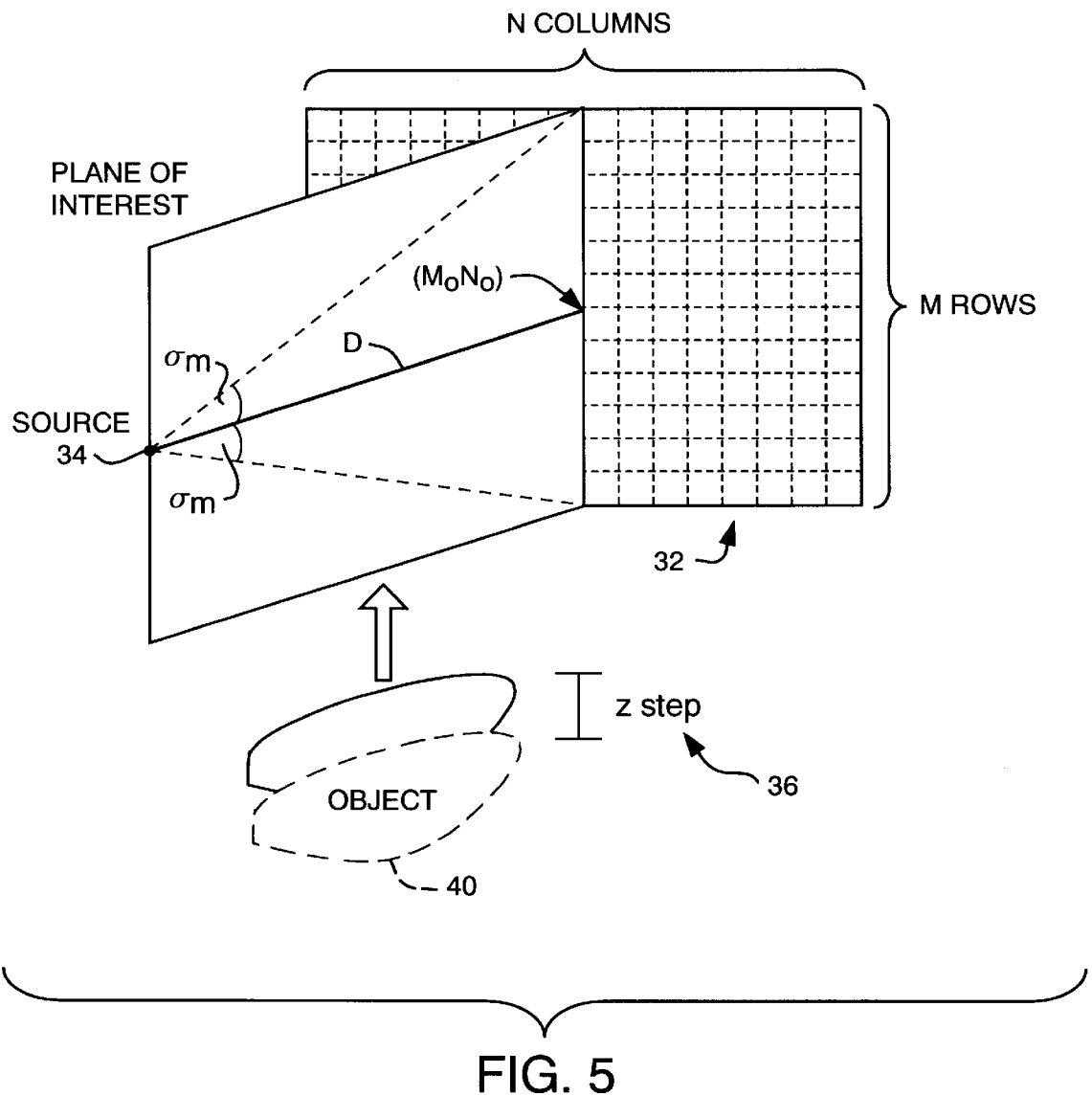
FIG. 5 depicts incremental processing steps performed in the z-direction by the system of FIG. 1.
Figure 6:
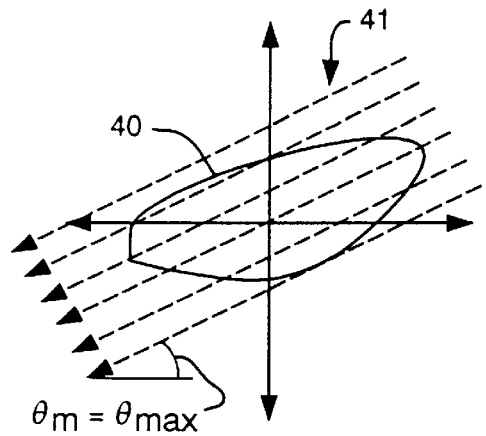
FIG. 6 depicts a set of parallel projection data at the $\theta_{max}$ angle (obtained from the $M^{th}$ row of the detector array as depicted in FIG. 5)
Figure 7:
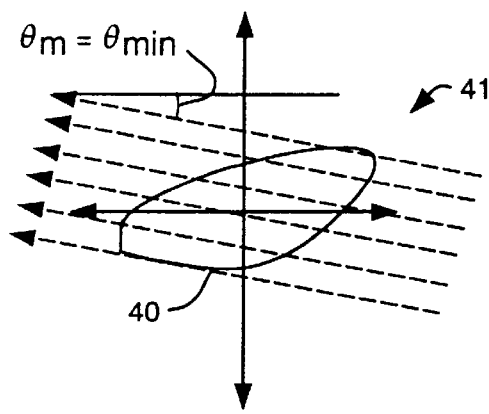
FIG. 7 depicts a set of parallel projection data at the $\theta_{min}$ angle (obtained from the first row of the detector array as depicted in FIG. 5)

FIG. 5 shows that the linear scanning orbit may be implemented by holding an x-ray source 34 and a detector panel 32 stationary, while moving object 40 along the z-axis 36 (which is also the rotational axis of the circular orbit). The object 40 is shown to move in the "z direction" in discrete increments identified at "z_step" 36 increments. Each vertical column of detectors 32 together with the source 34 defines a plane through the object 40. Within each vertical plane, every detector position defines a specific angle and the data collected by that detector corresponds to a parallel projection of the object sampled by intervals of z-step 36. FIG. 6 shows a number of parallel projections of object 40 at angle $\theta_m = \theta_{max}$ and FIG. 7 shows parallel projections of object 40 at angle $\theta_m = \theta_{min}$. These parallel projections are used to fill in the corresponding missing angular segment in the 2D FT plane. $\theta_{max}$ and $\theta_{min}$ are angles selected so that the data volume for the shadow cone 30 (FIG. 3) used to replace the shadow zone 28 data volume encompasses the shadow zone data volume. This condition is satisfied when $\theta_0 = \theta_m$, as illustrated in FIG. 2, where $$\theta_0 = \sin^{-1}\left(\frac{R}{d}\right),$$

wherein "R" is the radius of the smallest sphere containing object 40 and "d" is the radius of the circular orbit.

The shadow cone 30 (FIG. 3) in 3D Fourier space may be projected as a 2D shadow cone onto a set of 2D Fourier planes. The inverse transform of each of these 2D Fourier planes corresponds to an image plane defined by the x-ray source and a column "N" of detectors 32 (FIG. 5).

First, let F(u,v) be the Fourier transform of a 2D function f(x,y). The 1D Fourier data on $x=x_0$ is derived as follows:

$$F_{x_0}(v) = \int F(u,v)e^{j2\pi x_0 u} du \quad (2)$$

$$= \int\left\{\int\int f(x,y)e^{-j2\pi(xu+yv)}dx dy\right\}e^{j2\pi x_0 u}du$$

$$= \int\int f(x,y)e^{-j2\pi yv}\left\{\int e^{-j2\pi(x-x_0)u}du\right\}dx dy$$

$$= \int\int f(x,y)\delta(x-x_0)e^{-j2\pi yv}dx dy$$

$$= \int f(x_0, y)e^{-j2\pi yv}dy.$$

Similarly, for the Fourier transform of a 3D function f(x, y, z), the 2D Fourier transform of the object slice at $x=x_0$ is identified as follows:

$$F_{x_0}(v,w) = \int F(u,v,w)e^{j2\pi x_0 v}du \quad (3)$$

$$= \int\left\{\int\int f(x,y,z)e^{-j2\pi(xu+yv+zw)}dx dy dz\right\}e^{j2\pi x_0 u}du$$

$$= \int\int f(x,y,z)e^{-j2\pi(yv+zw)}\left\{\int e^{-j2\pi(x-x_0)u}du\right\}dx dy dz$$

$$= \int\int f(x,y,z)\delta(x-x_0)e^{-j2\pi(yv+zw)}dx dy dz$$

$$= \int f(x_0,y,z)e^{-j2\pi(yv+zw)}dy dz.$$

For the case when the desired "n" dimensional Fourier space is not orthogonal to the $(n+1)^{th}$ dimension of the augmented $(n+1)^{th}$ dimensional Fourier space. For example, if the desired 1D Fourier transform lies on a line defined by the equation $x \cos \theta + y \sin \theta - p = 0$, it is appropriate to rotate the original 2D coordinates, (x,y), into new coordinates, (x',y'), by angle $\theta$. Let F(u',v') be the Fourier transform of f(x',y'). Then F(u',v') is also obtained by rotating F(u,v) by the angle $\theta$. The Fourier transform along the line, $x \cos \theta + y \sin \theta - p = 0$, is identified as follows:

$$F_{x'-p}(v') = \int F(u',v')e^{j2\pi pu'}du'. \quad (4)$$

Similarly, the 2D Fourier transform along the plane defined by $x \cos \phi + y \sin \phi - \rho = 0$ is given by $$F_{x'-p}(v',w) = \int F(u',v',w)e^{j2\pi pu'}du'. \quad (5)$$

Figure 4A:
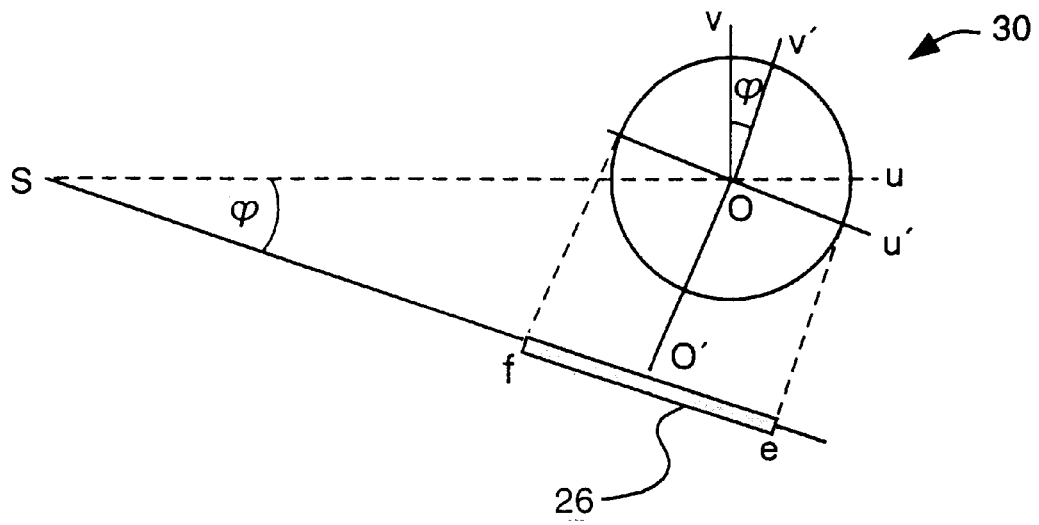
FIGS. 4a and 4b illustrate a cross-section of the shadow cone of FIG. 2 projected onto a plane.
Figure 4B:
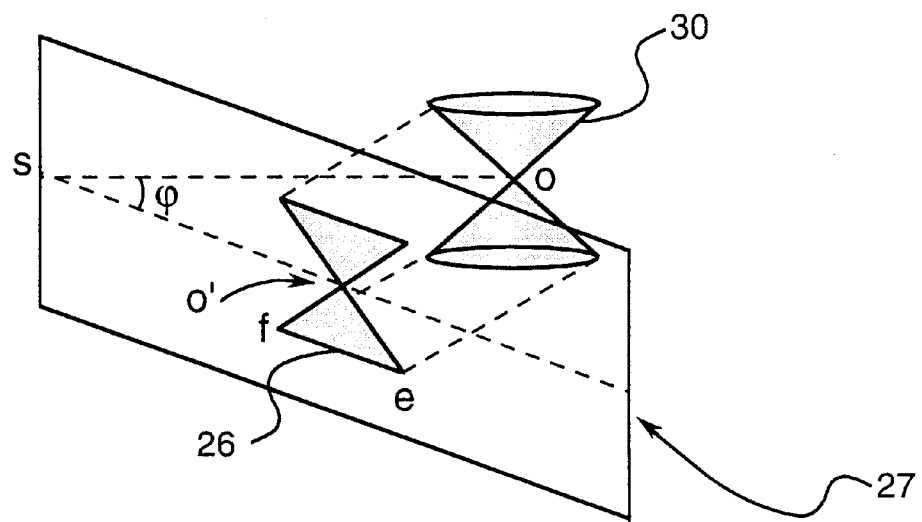

Again, F(u',v',w) is obtained by rotating the (u,v) coordinates by an angle φ, as illustrated in FIG. 4a, while keeping the w-coordinate unchanged. The rotated coordinate system is graphically illustrated in FIGS. 4a and 4b, where the new coordinates, (u',v',w), are chosen such that u' is parallel to the normal of the plane of interest (shown as the $\overrightarrow{SO'}$ line). As such, the shadow disc 26 (which is a cross-section of shadow cone 30 (FIG. 4a), intersecting a horizontal plane 27 (FIG. 4b), is projected onto $\overrightarrow{SO'}$ as a line segment centered at "O'" and having end points "f" and "e." The length of the line segment $\overline{fe}$ equals the diameter of the shadow cone 30 centered at "O."

In summary, shadow cone 30 (FIG. 4a), defining the area in Radon space in 3D Fourier space, is projected onto 2D Fourier subspace by applying a 1D inverse Fourier transform. In other words, rather than by replacing the shadow cone in 3D Fourier space, the scanned object 40 is represented in a series of 2D Fourier planes, and replaces the projected 2D shadow disc 26 in all the individual planes.

In applying the principle described above, the following array and scanner parameters will be assumed. Detector array 32 (FIG. 5) will be referred to by the expression, D(M×N), where the detector array 32 has "M" rows and "N" columns. Projection data of circular orbit will be referred to by the expression $P_C$(M×N×$V_C$), where $V_C$ is the total number of views. Projection data of the line orbit will be referred to by the expression $P_l$(M×N×$V_l$), where $V_l$ is also the total number of views. An image reconstructed from circular orbit data will have the form, $I_C$(K×K×K) or $I_{CS}$ (K×N×K); the former is a cubic volume, while the latter is a "horn-shaped" volume defined by the x-ray source and the detector panel. An image reconstructed from line orbit data will have the form, $I_l$(K×K×K) or $I_{lS}$(K×N×K); likewise, the former is a cubic volume and the latter is a "horn-shaped" volume.

The image is reconstructed from the line-orbit data. As a first step, the line-orbit projection data is modified to accommodate the effect of divergence as a plurality of rays passes from source 34 to detector array 32, as graphically illustrated in FIGS. 5, 6, and 7. The divergent ray detected on the detector panel is modified by multiplying the detector values with a weighting function as follows:

$$W(m, n) = \frac{D}{\sqrt{D^2 + (m - m_0)^2 a^2 + (n - n_0)^2 b^2}},$$

where "D" in this case is the source-to-detector distance (FIG. 5), and wherein $\overline{ISO}$ is projected onto $(m_0, n_0)$ of the detector panel 32. The values "a" and "b" are the detector pitches in the row and column dimensions, respectively. Detector pitches are standard definitions defining the distance between the centers of two adjacent detectors.

The $n^{th}$ angular vertical plane is reconstructed next. To reconstruct the $n^{th}$ angular vertical plane, the projection data, $P_{ln}$(M×$V_1$), is extracted from the $n^{th}$ column of the $P_l$ array, where the $m^{th}$ row corresponds to a fixed beam angle of $\theta_m$.

The row elements of $P_m$ are shifted such that the object center of this vertical slice is realigned at $$v = \frac{V_1}{2}.$$

Let $P'_{ln}$ be the realigned projection array.

To return to object space, either one of two methods may be taken. As a first option, apply a 1D FFT to each row of $P'_{ln}$. Place each set of FFT data on a radial line at an angle $\theta_m$ for m 1 ... M. An inverse FFT is utilized to convert the Fourier data set to object space.

As a second option the filtered $P'_{ln}$ for all "N" columns are back-projected to obtain a horn-shape volume comprising "N" vertical planes defined by the x-ray source 34 and "N" detector columns "N." Let $f_n(x,y)$ be the reconstructed image based on the $n^{th}$ column, and $Q_n$ the filtered projection array, then $$f_n(x, y) = \frac{|\theta_M - \theta_1|}{M} \sum_{m=1}^{M} Q_{nm}(x\cos\theta_m + y\sin\theta_m). \qquad (6)$$

The results of applying the above equation to the shifted row elements are identified as a volumetric array $I_{ls}$, having a horn shape.

The final image may be reconstructed by one of two possible methods. First, the shadow cone 30 may be replaced in 3D Fourier space. Alternatively, the shadow cone 30 may be replaced in 2D Fourier spaces and then interpolated from the horn shape volume back to cubic volume.

The replacement of the shadow cone 30 in 3D space is presented first. As a first step, the Feldkamp algorithm is used to reconstruct the image, $I_C$, associated with torus 24, from the circular orbit data. Next, a 3D Fourier transform, $F(I_C)$, is obtained from $I_C$.

The horn shaped volume, $I_{ls}$, is interpolated to obtain a corresponding cubic volume, $I_l$. A 3D Fourier transform, $F(I_l)$ is obtained from $I_l$.

The shadow cone portion of $F(I_C)$ is replaced with its counterpart from $F(I_l)$ to provide a repaired Fourier data array. An inverse Fourier transform is then applied to the repaired Fourier data array to return to cubic space.

Replacing the shadow cone in 2D Fourier spaces is presented next. As a first step, the Feldkamp algorithm is again used to reconstruct image $I_C$ from the circular orbit data. Next, $I_C$ is interpolated to $I_{CS}$, in which $I_S$ defines a plurality of angular vertical planes. $I_{ls}$ is obtained from the line orbit data, as described above.

The Fourier transform $F(I_{CS})$ and $F(I_{l_S})$ is obtained from $I_{CS}$ and $I_{l_S}$. The shadow cone is substituted into each 2D plane of $F(I_{CS})$, with its counterpart defined in $F(I_{l_S})$. An inverse Fourier transform is applied to each of the repaired 2D sets of Fourier data. Finally, the horn-shape volume is interpolated back to cubic volume.

The DFM method described above requires interpolation from polar coordinates to rectangular coordinates.

The cone beam reconstruction described above is based on circle and line orbits which requires that the missing shadow zone 28 of circle orbit data in the Fourier domain to be replaced by the line orbit data. For the line orbit orientation illustrated in FIG. 5, the object 40 is shown to move in the "z direction" in discrete increments identified as "z_step" 36 increments. Each vertical column of detectors 32 together with the source 34 defines a plane through the object 40. Within each vertical plane, every detector position defines a specific angle and the data collected by that detector corresponds to a parallel projection of the object sampled by intervals of z-step (FIGS. 5, 6, and 7). FIG. 6 shows a number of parallel projections of object 40 at angle $\theta_m = \theta_{max}$ and FIG. 7 shows parallel projections of object 40 at angle $\theta_m = \theta_{min}$. These parallel projections are used to fill in the corresponding missing angular segment in the 2D FT plane. $\theta_{max}$ and $\theta_{min}$ are angles selected so that the data volume for the shadow cone 30 (FIG. 3) used to replace the shadow zone 28 data volume encompasses the shadow zone data volume. This condition is satisfied when $\theta_0=\theta_m$, as illustrated in FIG. 2.

One approach is to reconstruct the filtered back-projection (FBP) image for each angular plane using the parallel projections from the set of limited angular views and then to compute the 2D FT and use it to replace the missing angular segment.

Another alternative is to convert the polar grid data from 1D FT of parallel projections to rectangular grid directly in 2D FT domain. This method is similar to the interpolation required in Direct Fourier Method back-projection.

In the line orbit, for each plane, a number of projections (equal to "M" detectors in each vertical column) are acquired, for an angular range from $\theta_{min}$ to $\theta_{max}$. Interpolation techniques for the line data provide the methodology for developing the below described interpolation techniques that are useful for calculating the cone beam reconstruction methods.

First, let $\mu_\phi(x, y)$ be the image in a fixed coordinate system x-y and $\mu_\phi(\hat{x}, \hat{y})$ represent the object in a coordinate system $\hat{x}$-$\hat{y}$ rotated from x-y by an angle $\phi$. The projection of the object at a view angle $\phi$ is $$P_\phi(\hat{x}) = \int \mu_\phi(\hat{x},\hat{y})d\hat{y}. \tag{7}$$

The 1D FT of $p_\phi(\hat{x})$ is given as $$P_\phi(u) = \int p_\phi(\hat{x}) e^{-j2\pi \hat{x}u} \, du. \tag{8}$$

If $M_\phi(\rho, \phi)$ denotes the 2D FT of $\mu_\phi(x, y)$ in polar coordinates, then based on the Projection slice theorem, $$M(\rho, \phi) = P_\phi(\rho), \text{ where}$$

$$\rho > 0, \, 0 \leq \phi < 2\pi \tag{9}$$

Assuming that $M(\rho, \phi)$ is known, this FT data on polar coordinates may be converted to Cartesian coordinates by the expression, $M(\rho \cos \phi, \rho \sin \phi) = M(\rho, \phi)$. The object is reconstructed by 2D inverse FT using the expression, $$\mu(x, y) = \int M_C(u, v) e^{-j2\pi(ux+vy)} \, du \, dy. \tag{10}$$

However, $M(\rho, \phi)$ is not known at all positions but only at finite set of discrete points $(\rho_j, \phi_k)$. The problem then becomes interpolating from the known values of polar points to the values requires over a rectangular Cartesian grid.

An existing theorem is utilized to solve this problem. First, let x(t) be a periodic function in time space "t" with period "T." If x(t) is angularly band-limited to a value $$\left(c\frac{1}{T}\right)$$

where "c" is a constant, and "K" is an integer relating to the number of samples of x(t), then x(t) can be written as:

$$x(t) = \sum_{l=0}^{2K+1} x(lT_S) \frac{\sin\left[\frac{\pi}{T}(t - lT_S)\right]}{(2K+1)\sin\left[\frac{\pi}{T}(t - lT_S)\right]}, \tag{11}$$

where $T_S = \dfrac{T}{2K+1}$.

The proof follows from Shannon's sampling theorem as follows:

$$x(t) = \sum_{n=-\infty}^{\infty} x(nT_S) \text{sinc}\left[\frac{1}{T_S}(t - nT_S)\right] \tag{12}$$

$$= \ldots + \sum_{l=0}^{N-1} x((l-N)T_x) \text{sinc}\left[\frac{1}{T_S}(t - (l-N)T_x)\right] +$$

$$\sum_{l=0}^{N} x(lT_S) \text{sinc}\left[\frac{1}{T_S}(t - lT_x)\right] +$$

$$\sum_{l=0}^{N-1} x((l+N)T_S) \text{sinc}\left[\frac{1}{T_S}(t - (l+N)T_x)\right] + \ldots \tag{13}$$

$$= \sum_{l=0}^{N-1} x(lT_S) \text{sinc}\left[\frac{1}{T_S}(t - (lT_S + kT))\right]$$

were the number of data array columns N=2K+1.

Angular interpolation employs the function $M(\rho, \phi)$ wherein variable $\phi$ has a period of $2\pi$. Since $M(\rho, \phi)$ is angularly band-limited to "K" (i.e., Fourier series coefficients satisfy $c_n = 0$ for $|n| > K$), then $$M(\rho, \phi) = \sum_{k=0}^{2K+1} M\left(\rho, \frac{k\pi}{K+1}\right) \sigma\left(\phi - \frac{k\pi}{K+1}\right), \tag{14}$$

$$\text{where } \rho(\phi) = \frac{\sin\left(\frac{2K+1}{2}\phi\right)}{(2K+1)\sin\left(\frac{1}{2}\phi\right)}. \tag{15}$$

Radial interpolation is described next. If the object is space limited to diameter 2A, where "A" is equivalent to radius "R", identified previously as the radius of the smallest sphere containing the object 40, its projections are also limited to diameter 2A and therefore the FT of the projection $P\phi(u)$ can be reconstructed as $$P_\phi(u) = \sum_{n=-\infty}^{\infty} P_\phi\left(\frac{n}{2A}\right) \text{sinc}\left[2A\left(u - \frac{n}{2A}\right)\right], \tag{16}$$

using Shannon's sampling theorem.

Combining angular and radial interpolation:

$$M(\rho, \phi) = \sum_{n=-\infty}^{\infty} \sum_{k=0}^{2K+1} M\left(\frac{n}{2A}, \frac{k\pi}{K+1}\right) \text{sinc}\left(2A\left(\rho - \frac{n}{2A}\right)\right) \sigma\left(\phi - \frac{k\pi}{K+1}\right). \tag{17}$$

$M_C(u_l, v_m)$ is computed over the Cartesian space as:

$$M_C(u_l, v_m) = M\sqrt{u_m^2 + v_m^2}, \cos^{-1}\frac{u_m}{\sqrt{u_m^2 + v_m^2}}. \tag{18}$$

To reduce interpolation error, a number of steps may be taken, as described below. Error from inadequate sampling in space will be considered first.

During the line orbit, the parallel projection data are sampled in intervals of a predetermined z-step 36. As the projections are space limited they will not be band-limited. Sampling the projections over a predetermined z-step window (for example 2A) will effectively reduce the bandwidth and introduce aliasing artifacts into the 2D FT domain. Consequently, the "z_step" 36 is selected to be small enough such that the effective bandwidth, $$B = \frac{1}{2 * z\_step}$$

[points/cycle], will substantially include the frequency content of the projections.

Another source of error is inadequate sampling in a radial frequency. If the object is space limited in diameter to $$\frac{1}{2*A},$$

its projections will also be space limited to 2A, as such, the FT is sampled uniformly at intervals of at least, $$\frac{1}{2A}$$

[points/cycle], in order to avoid aliasing.

For the line data, the effective bandwidth is defined as "B." The number of radial samples "N" are chosen such that $$\frac{2*B}{N} = \frac{1}{N*z\_step} \leq \frac{1}{2*A}.$$

Also the grid spacing in the 2D FT domain is at most $$\frac{1}{2A}$$

[points/cycle].

Another source of error is an insufficient number of views. Non-isotropic and off-centered objects will not be angularly band-limited. So, the number of projections may be very large. However, in practice the number of projections is chosen such that in the 2D FT domain the sampling between two neighboring radial lines will be approximately equal to the maximum grid spacing of $$\frac{1}{2A}$$

[points/cycle].

Interpolation in the 2D FT domain is described next. For the line orbit data, a rectangular grid spacing of $$\frac{1}{2A}$$

[points/cycle], is used in the 2D FT domain. In a computer implementation, typically, the Fast Fourier Transform (FFT) is used for computing the 1D FT of each projection. In order to improve radial sampling, zero padding of the projection data is performed before applying FFT. In this specification zero padding involves the steps of adding zeros to the data set to minimize artifacts after an FFT is performed. Once a radial sampling has been obtained, Nearest neighbor interpolation or Linear interpolation is used to compute the values between the new sample points.

As mentioned previously, for the line orbit a plurality of projections are required for a small angular segment (i.e., angular direction is over-sampled compared to radial sampling). One concern is how to use this data efficiently. A simple interpolation scheme such as nearest neighbor will not use all of the available data. One alternative approach is to decimate the number of views by grouping the rows and then summing the rows from each group so as to increase the signal to noise ratio (SNR) utilizing an inverse bilinear interpolation technique, as further described below.

In the present invention, an inverse bilinear interpolation technique is used on data in the polar grid format. For optimal interpolation in the azimuthal direction, $\sigma(\phi)$ the function defined in equation (13) may be used. However, this function is computationally impractical. For a computer implementation, values in the interpolation function must be truncated which causes artifacts.

From a computational standpoint, the simplest interpolation algorithm to implement is the Nearest neighbor (NN) algorithm, wherein each pixel is given the value of the sample which is closest to the pixel. NN is equivalent to convolving the sampled data by a rectangular function. Convolution with a rectangle function in the spatial domain is equivalent to multiplying the signal in frequency domain by a sinc(.) function, which is a poor low pass filter since it has prominent side lobes.

Linear interpolation amounts to convolution of the sampled data by a triangle window. This function corresponds in frequency domain to a $\text{sinc}^2(.)$ function which has a better low pass filtering property than NN.

The NN method interpolates on the basis of a single point. The linear interpolation algorithm interpolates on the basis of two nearest points. Using three points for interpolation would result in two points on one side and only one on the other side. The B-spline method enables interpolation over the two nearest points in each direction. The Cubic B-spline method comprises four convolutions of the rectangular function of the NN method. Since Cubic B-splines are symmetric, they only need to be defined in the interval (0, 2). Mathematically, the B-splines can be written as:

$$f(x) = x^3 - x^2 + \frac{4}{6} \qquad x \in (0, 1)$$

$$f(x) = \frac{-x^3}{6} + x^2 - 2x + \frac{8}{6} \qquad x \in (1, 2)$$

The Cubic B-splines equations defined above may be adapted to fit a smooth third-order polynomial through the available set of shadow cone 30 data.

Another interpolation function involves the truncation of $\sigma(\phi)$. As mentioned previously, it is desirable to find the ideal interpolation function in the angular direction of the $\sigma(\phi)$ function. However, the $\sigma(\phi)$ function has considerable energy and, as such, does not decay fast over an extended distance, and therefore cannot be easily implemented as a space domain convolution. It is natural to truncate the function over a small distance, but truncation disregards much of the above said energy. Moreover, truncation in the space domain will produce ringing artifacts when the object is converted from the space domain to the signal domain.

Bilinear interpolation is a 2D interpolation method. In this interpolation method f(x,y) is evaluated by a linear combination of $f(n_1, n_2)$ at the four closest points for $n_1 T \leq x \leq (n_1+1)T$ and $n_2 T \leq y \leq (n_2+1)T$. The interpolated value f(x,y) in the bilinear method is:

$$f(x, y) = (1 - \Delta_x)(1 - \Delta_y)f(n_1, n_2) + (1 - \Delta_x)\Delta_y f(n_1, n_2 + 1) +$$
$$\Delta_x(1 - \Delta_y)f(n_1 + 1, n_2) + \Delta_x\Delta_y f(n_1 + 1, n_2 + 1)$$
$$\text{where } \Delta_x = \frac{(x - n_1 T)}{T} \text{ and } \Delta_y = \frac{(y - n_2 T)}{T}.$$

Inverse bilinear interpolation converts polar-grid data into rectangular-grid data via inverse bilinear weighting. That is, each polar-grid element is redistributed to its four nearest rectangular grids using the four sub-areas as normalized weights. The method is robust in the sense that the original data does not have to be regularly distributed, as long as the data has at least one element in each rectangular square. As such, undesirable data elements caused by defects or seams in detector array 32 (FIG. 5) may be ignored. Another benefit of this process is that all the good data are fully utilized, which, consequently, provides a better signal-to-noise ratio (SNR).

Figure 8:
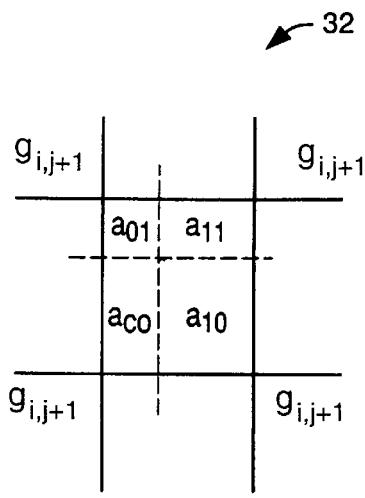
FIG. 8 depicts inverse bilinear interpolation of the system of FIG. 1.

A linear orbit datum value "x" and associated grid points used in inverse bilinear interpolation are graphically illustrated in FIG. 8. The data value "x" is distributed to its four nearest grid points as follows:

$$g_{i,j} = g_{i,j} + a_{11}x$$
$$g_{i+1,j} = g_{i+1,j} + a_{01}x$$
$$g_{i,j+1} = g_{i,j+1} + a_{10}x$$
$$g_{i+1,j+1} = g_{i+1,j+1} + a_{00}x$$

Each grid point has an accumulated value, $g_{ij}$, which identifies the accumulated weighted "x" values from the four adjacent squares. To normalize the accumulated value at each grid point, it is necessary to maintain another variable, $w_{ij}$, which identified the accumulated weights ($a_{ij}$) associated with the bilinear distribution of pixel (I,j). In fact, this is a normalization step at the end of the interpolation procedure because each grid value is divided by accumulated weight, $w_{ij}$.

Six sets of simulations were conducted using the described interpolation methods for the 2D FT domain and the image domain. The simulation results illustrate Inverse bilinear interpolation as compared to Nearest neighbor (NN), Linear, Cubic B-Spline, and Filtered back projection (FBP) interpolation methods. Results are presented in Tables I through VI.

For the first three simulations, Linear interpolation was used in the radial direction. Nearest neighbor, Linear and Cubic B-spline interpolation techniques were used in the azimuthal direction. The reconstruction of an angular segment in the 2D FT domain was simulated using the line orbit data. The slice of interest was the central slice through the object in FIG. 5. The object consisted of three horizontal disks so that it had sharp edges in z (vertical) direction.

The Truncated σ(φ) interpolation method was also used in the azimuthal direction (including 8 neighboring points). Linear interpolation was used in the radial direction. Nearest neighbor interpolation and Linear interpolation generated better performance results than Cubic B-spline interpolation. However, Cubic B-spline uses only 4 points as opposed to 8 points in Truncated σ(φ) interpolation. So, Cubic B-spline is computationally more attractive than the 8 points Truncated σ(φ) interpolation, as such, Truncated σ(φ) interpolation was not included in the comparison.

Polar points based bilinear interpolation was also evaluated. The 2D FT of the slice of interest was computed and used as the base reference for of comparing the above identified methods. The 2D FT of the FBP reconstruction was also included in the comparison. FBP reconstruction requires the reconstruction of the 2D FMP image and then computation of the 2D FT. However, Polar bilinear interpolation does not require conversion back to the image domain. This results in a computational advantage over the FBP method.

In order to measure the performance of each method, the interpolated rectangular grid values were computed using the above methods for different numbers of views and radial samples. The error was computed with the true 2D FT as follows: Norm1 (total absolute difference, Table I); Norm2 (square root of the total squared distance, Table II); and Norm∞ (maximum absolute difference, Table III). Note, that terms Norm1, Norm2, and Norm∞ are standard terms used in statistical analysis.

TABLE I

| | % NORM1 ERROR in 2D FT DOMAIN | | | |
|---|---|---|---|---|
| # of views | 256 | 256 | 64 | 16 |
| # of radial samples | 1280 | 256 | 256 | 256 |
| Near. Neigh. | 58.4 | 58.0 | 60.9 | 75.2 |
| Linear | 49.7 | 49.5 | 51.6 | 67.1 |
| Cubic B-Spline | 45.7 | 45.6 | 47.9 | 64.9 |
| Inverse bilinear | 41.2 | 40.7 | 43.3 | 60.9 |
| FBP | 77.6 | 77.6 | 77.6 | 77.6 |

TABLE II

| | % NORM2 ERROR in 2D FT DOMAIN | | | |
|---|---|---|---|---|
| # of views | 256 | 256 | 64 | 16 |
| # of radial samples | 1280 | 256 | 256 | 256 |
| Near. Neigh. | 31.6 | 31.6 | 33.0 | 38.9 |
| Linear | 26.5 | 26.5 | 26.3 | 33.8 |
| Cubic B-Spline | 24.4 | 24.5 | 24.8 | 32.9 |
| Inverse bilinear | 21.8 | 21.3 | 22.4 | 31.9 |
| FBP | 54.5 | 54.5 | 54.5 | 54.5 |

TABLE III

| | % NORM∞ ERROR in 2D FT DOMAIN | | | |
|---|---|---|---|---|
| # of views | 256 | 256 | 64 | 16 |
| # of radial samples | 1280 | 256 | 256 | 256 |
| Near. Neigh. | 8.88 | 8.88 | 8.88 | 8.88 |
| Linear | 8.87 | 8.87 | 7.82 | 6.78 |
| Cubic B-Spline | 8.61 | 8.61 | 7.70 | 6.77 |
| Inverse bilinear | 7.58 | 6.08 | 6.08 | 7.26 |
| FBP | 80.25 | 80.25 | 80.25 | 80.25 |

The corresponding limited view images were also computed (Tables IV–VI) using inverse 2D FT from the interpolated rectangular grids. The errors were compared in the reconstructed images with the true image. The FBP image are also included in the comparison. Note that in the real implementation for the line orbit, it is not necessary to reconstruct the images before patching the 2D FT data into the Feldkamp 2D FT data.

TABLE IV

| | % NORM1 ERROR in IMAGE DOMAIN | | | |
|---|---|---|---|---|
| # of views | 256 | 256 | 64 | 16 |
| # of radial samples | 1280 | 256 | 256 | 256 |
| Near. Neigh. | 24.1 | 24.0 | 24.2 | 27.4 |
| Linear | 19.1 | 19.1 | 18.4 | 21.2 |
| Cubic B-Spline | 16.1 | 16.1 | 15.7 | 18.9 |
| Inverse bilinear | 12.5 | 11.8 | 12.5 | 22.3 |
| FBP | 38.5 | 38.5 | 38.5 | 38.5 |

TABLE V

| | % NORM2 ERROR in IMAGE DOMAIN | | | |
|---|---|---|---|---|
| # of views | 256 | 256 | 64 | 16 |
| # of radial samples | 1280 | 256 | 256 | 256 |
| Near. Neigh. | 93.3 | 93.1 | 87.5 | 108.4 |
| Linear | 52.8 | 52.6 | 50.1 | 77.6 |
| Cubic B-Spline | 50.8 | 50.7 | 49.4 | 75.7 |
| Inverse bilinear | 40.0 | 40.3 | 45.8 | 89.9 |
| FBP | 84.5 | 84.5 | 84.5 | 84.5 |

TABLE VI

| | % NORM∞ ERROR in IMAGE DOMAIN | | | |
|---|---|---|---|---|
| # of views | 256 | 256 | 64 | 16 |
| # of radial samples | 1280 | 256 | 256 | 256 |
| Near. Neigh. | 82.0 | 81.7 | 93.8 | 133.5 |
| Linear | 67.8 | 67.5 | 78.4 | 121.5 |
| Cubic B-Spline | 66.5 | 66.2 | 77.7 | 117.0 |
| Inverse bilinear | 61.8 | 61.8 | 68.0 | 89.3 |
| FBP | 97.8 | 97.8 | 97.8 | 97.8 |

It may be observed that increasing the radial sampling does not reduce the error in the image domain. However, decreasing the radial sampling does introduce errors because the rectangular grid spacing are no longer on the same order as radial sampling. However, the value of the "z step" 36 is fixed because of bandwidth constraints. Thus, "N" samples are available for each projection such that N multiplied by "z_step"=2A.

In each case the inverse bilinear interpolation has less error both in the 2D FT domain and in the image domain compared to the other listed interpolation methods. The number of views in the 2D FT domain and the image domain may also be reduced from 256 without significantly increasing the image error as, for example, can be observed by the data in Table VI.

Specific embodiments of various methods and apparatuses of reconstructing CT images according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

What is claimed is:

1. A method of reconstructing x-ray tomographic images comprising data from a circular orbit and data from a linear orbit, based on a shadow zone formed by projecting data of the circular orbit, such method comprising the steps of:

representing the image obtained from the circular orbit in a circular horn-shaped volume;

representing the image obtained from the linear orbit in a corresponding linear horn-shaped volume;

converting 2D images in the vertical planes of each said circular horn-shaped volume and each said linear horn-shaped volume into a plurality of 2D Fourier planes;

removing projections of a 3D shadow cone in each of said 2D Fourier planes from the circular orbit data and replacing said projections with the corresponding projections obtained from the linear orbit data, so as to generate a plurality of repaired 2D Fourier planes;

conducting an inverse 2D Fourier Transform on said plurality of repaired 2D Fourier planes to obtain a respective plurality of 2D image planes, representing a resulting horn-shaped volume; and converting said resulting horn-shaped volume back to the x-ray tomographic image.

2. The method as recited in claim 1, wherein said step of representing the image obtained from the circular orbit further comprises the step of selecting a shadow cone having a subtended angle of $2\theta_o$, wherein said angle $\theta_o$, is defined as the angle which identifies the limit of said shadow zone in radon space.

3. The method as recited in claim 1, wherein said step of representing the image obtained from the linear orbit further comprises the step of generating a plurality of vertical image slices from the linear orbit data to form said linear horn-shaped volume.

4. The method as recited in claim 3, wherein said step of generating a plurality of vertical image slices further comprises the step of reconstructing a plurality of parallel beams generated from a projection of the linear orbit data.

5. The method as recited in claim 4, further comprising the step of using a filtered back-projection method to reconstruct said plurality of vertical image slices.

6. The method as recited in claim 4, further comprising the step of using a Direct Fourier Method to reconstruct said plurality of vertical image slices.

7. The method as recited in claim 6, wherein said step of using a Direct Fourier Method, further comprises the step of using inverse bilinear interpolation to convert data from the polar grid to the rectangular grid.

8. The method as recited in claim 7, wherein said step of performing inverse bilinear interpolation further comprises the step of performing inverse bilinear interpolation on each line orbit Fourier datum value "x" with respect to the four nearest grid locations, $g_{ij}$, $g_i+1_j$, $g_{ij}+1$ and $g_i+1_j+1$.

9. The method as recited in claim 8, wherein said step of performing inverse bilinear interpolation on each said line orbit datum value, "x," further comprises the step of determining a normalized sub-area, $a_{00}$, $a_{01}$, $a_{10}$, $a_{11}$, between a location of each respective said line orbit datum value "x," and each of the said four nearest grid locations, $g_{ij}$, $g_i+1_j$, $g_{ij}+1$ and $g_i+1_j+1$.

10. The method as recited in claim 9, further comprising the step of collecting for each grid point, $g_{i,j}$, adjacent to a respective said line orbit datum value, "x" and assigning a weight, $w_{ij}$.

11. The method as recited in claim 10, wherein said step of determining a normalized sub-area further comprises the step of updating each said grid location according to the following equalities:

$$g_{ij} = g_{ij} + a_{11}x$$

$$g_{i+1,j} = g_{i+1,j} + a_{01}x$$

$$g_{i,j+1} = g_{i,j+1} + a_{10}x$$

$$g_{i+1,j+1} = g_{i+1,j+1} + a_{00}x.$$

12. The method as recited in claim 11, further comprising the step of normalizing each grid data, $g_{ij}$ by dividing a respective $g_{ij}$ by $w_{ij}$.

13. An apparatus for reconstructing x-ray tomographic images comprising data from a circular orbit and data from a linear orbit, based on a shadow zone formed by projecting data of the circular orbit, such apparatus comprising:

means for representing the image obtained from the circular orbit in a circular horn-shaped volume;

means for representing the image obtained from the linear orbit in a corresponding linear horn-shaped volume;

means for converting 2D images in the vertical planes of each said circular horn-shaped volume and each said linear horn-shaped volume into a plurality of 2D Fourier planes;

means for removing projections of a 3D shadow cone in each of said 2D Fourier planes from the circular orbit data and replacing said projections with the corresponding projections obtained from the linear orbit data, so as to generate a plurality of repaired 2D Fourier planes;

means for conducting an inverse 2D Fourier Transform on said plurality of repaired 2D Fourier planes to obtain a respective plurality of 2D image planes, representing a resulting horn-shaped volume; and means for converting said resulting horn-shaped volume back to the x-ray tomographic image.

14. The apparatus as recited in claim 13, wherein said means for representing the image obtained from the circular orbit further comprises means for selecting a shadow cone having a subtended angle of $2\theta_o$, wherein said angle $\theta_o$, is defined as the angle which identifies the limit of said shadow zone in radon space.

15. The apparatus as recited in claim 13, wherein said means for representing the image obtained from the linear orbit further comprises means for generating a plurality of vertical image slices from the linear orbit data to form said linear horn-shaped volume.

16. The apparatus as recited in claim 15, wherein said means for generating a plurality of vertical image slices further comprises means for reconstructing a plurality of parallel beams generated from a projection of the linear orbit data.

17. The apparatus as recited in claim 16, further comprising means for using a filtered back-projection method to reconstruct said plurality of vertical image slices.

18. The apparatus as recited in claim 16, further comprising means for using a Direct Fourier Method to reconstruct said plurality of vertical image slices.

19. The apparatus as recited in claim 18, wherein said Direct Fourier Method means, further comprises means for using inverse bilinear interpolation to convert data from the polar grid to the rectangular grid.

* * * * *